United States Patent
Alzaga et al.

(10) Patent No.: US 11,166,719 B2
(45) Date of Patent: Nov. 9, 2021

(54) ENDOSCOPIC SURGERY SYSTEM CONSISTING OF A PLURALITY OF STAPLES AND AN ENDOSCOPIC APPLICATOR

(71) Applicant: INSTITUT HOSPITALO-UNIVERSITAIRE DE CHIRURGIE MINI-INVASIVE GUIDEE PAR L'IMAGE, Strasbourg (FR)

(72) Inventors: Amilcar Alzaga, Mexico City (MX); Pietro Riva, Cesano Maderno (IT)

(73) Assignee: Institut Hospitalo-Universitaire de Chirurgie Mini-Invasive Guidee Par L'Image S/C IRCAD, Strasbourg (FR)

( * ) Notice: Subject to any disclaimer, the term of this patent is extended or adjusted under 35 U.S.C. 154(b) by 240 days.

(21) Appl. No.: 15/549,595

(22) PCT Filed: Feb. 12, 2016

(86) PCT No.: PCT/FR2016/050330
§ 371 (c)(1),
(2) Date: Aug. 8, 2017

(87) PCT Pub. No.: WO2016/128693
PCT Pub. Date: Aug. 18, 2016

(65) Prior Publication Data
US 2018/0000482 A1 Jan. 4, 2018

(30) Foreign Application Priority Data
Feb. 13, 2015 (FR) ...................................... 1551204

(51) Int. Cl.
*A61B 17/072* (2006.01)
*A61B 17/064* (2006.01)
(Continued)

(52) U.S. Cl.
CPC .... *A61B 17/07207* (2013.01); *A61B 17/0644* (2013.01); *A61B 17/0684* (2013.01);
(Continued)

(58) Field of Classification Search
CPC ............ A61B 17/0684; A61B 17/0644; A61B 17/07207; A61B 2017/07278; A61B 2017/00296; A61B 2017/07271
See application file for complete search history.

(56) References Cited

U.S. PATENT DOCUMENTS 4,895,289 A * 1/1990 Richards ............ A61B 17/0684
227/141
5,114,065 A * 5/1992 Storace .............. A61B 17/0684
227/132
(Continued)

FOREIGN PATENT DOCUMENTS

EP 0713684 A2 5/1996

*Primary Examiner* — Thomas M Wittenschlaeger
(74) *Attorney, Agent, or Firm* — Harness, Dickey & Pierce, PLC

(57) ABSTRACT

An endoscopic surgery system includes a plurality of staples and an endoscopic applicator having a staple cartridge for loading transversely arranged staples. The staples have a central region and two side limbs and the applicator has a mobile body for holding a staple to be applied, the staple being arranged in a transverse plane, and for ensuring the deformation of same by bending in relation to the axis of symmetry of the staple.

11 Claims, 3 Drawing Sheets

(51) Int. Cl.
*A61B 17/068* (2006.01)
*A61B 17/00* (2006.01)

(52) U.S. Cl.
CPC ............... *A61B 2017/00296* (2013.01); *A61B 2017/07271* (2013.01); *A61B 2017/07278* (2013.01)

(56) References Cited

U.S. PATENT DOCUMENTS

| | | | | |
|---|---|---|---|---|
| 5,395,030 A * | 3/1995 | Kuramoto | ........... | A61B 1/00087 227/179.1 |
| 5,456,400 A * | 10/1995 | Shichman | ............ | A61B 17/064 227/176.1 |
| 8,133,240 B2 * | 3/2012 | Damarati | ............ | A61B 17/122 606/143 |
| 2007/0055292 A1 * | 3/2007 | Ortiz | ................ | A61B 17/00234 606/139 |
| 2008/0269803 A1 * | 10/2008 | Sater | .................. | A61B 17/0057 606/219 |
| 2009/0072006 A1 * | 3/2009 | Clauson | .............. | A61B 17/0684 227/176.1 |
| 2009/0272783 A1 * | 11/2009 | Crainich | ............ | A61B 17/0401 227/176.1 |
| 2009/0272786 A1 * | 11/2009 | Zeiner | .................. | A61B 17/068 227/179.1 |
| 2009/0275957 A1 * | 11/2009 | Harris | .................. | A61B 17/064 606/142 |
| 2011/0029015 A1 * | 2/2011 | Kamei | ................ | A61B 17/0684 606/219 |
| 2012/0211543 A1 * | 8/2012 | Euteneuer | .......... | A61B 17/0642 227/175.1 |
| 2013/0245642 A1 * | 9/2013 | Souls | ................. | A61B 17/0684 606/139 |
| 2014/0263560 A1 * | 9/2014 | Chase | ................ | A61B 17/0684 227/177.1 |
| 2015/0133966 A1 * | 5/2015 | Gupta | ................ | A61B 17/0644 606/142 |
| 2016/0106420 A1 * | 4/2016 | Foerster | ............ | A61B 17/0644 606/219 |

* cited by examiner

ENDOSCOPIC SURGERY SYSTEM CONSISTING OF A PLURALITY OF STAPLES AND AN ENDOSCOPIC APPLICATOR

CROSS-REFERENCE TO RELATED APPLICATIONS

This application is a National Phase Entry of International Patent Application Serial Number PCT/FR2016/050330, filed on Feb. 12, 2016, which claims priority to French Patent Application Serial No. 15/51204, filed on Feb. 13, 2015, both of which are incorporated by reference herein.

TECHNICAL FIELD

The present invention relates to the field of endoscopic staple applicators. Such an applicator enables the surgeons to place staples in order to hold tissues during endoscopic surgery. An endoscopic staple applicator is designed to hold a plurality of staples, in particular ligature staples, in a staple channel and a system of jaws used to apply a staple. The jaw system is connected to the distal end of the staple channel and to the proximal end of a control handle.

BACKGROUND

In the prior art, U.S. Pat. No. 8,133,240 is known, describing an endoscopic stapling system. This system comprises deformable staples disposed end to end in a cavity of an interior channel. Runners slide inside this channel under the action of a thrust element. When it is ejected, the staple deforms in order to clamp the body tissue.

The patent EP 0713684 is also known, describing a system formed by a cartridge of staples and a stapling instrument for applying one or more surgical staples to a tissue. Each staple has a body in the rough form of a U comprising a top cross member having adjacent staple lugs on the opposite sides of the top crossmember. A cartridge housing receiving a plurality of staples is arranged in a row so that they have a longitudinal movement through it. An anvil is mounted on said housing. The staple furthest forward is moved until it is in contact with said anvil and then tilted from a transverse orientation to a longitudinal orientation, and then deformed by pressure on said anvil in order to fix the staple.

The solutions of the prior art are not completely satisfactory since they generally provide for a positioning of the staple applied in the transverse plane, which reduces the opening of the points of the staple hooking onto the edges of the tissues to be held. Moreover, the staple loader often has a fairly large longitudinal dimension, making the solution unsuitable for use with flexible endoscopes. Finally, the solutions of the prior art generally mask a major part of the endoscopic field of vision, which makes these tricky operations particularly difficult.

SUMMARY

In order to remedy these drawbacks, the present invention relates, in its most general acceptance, an endoscopic surgery system formed firstly by a plurality of staples and secondly by an endoscopic applicator comprising a staple loader disposed transversely, characterised in that said staples have a central zone and two lateral arms and in that the applicator comprises a movable member having a means for holding, in a transverse frame, a staple to be applied and for ensuring deformation thereof by folding with respect to the symmetry axis of said staple. Advantageously, the control member is formed by a rigid hollow tubular sleeve and a rigid rod sliding longitudinally inside this sleeve, having a guide channel with a complementary cross section. Preferably, said rigid rod has a polygonal cross section complementary to the cross section of said guide channel provided in the sleeve.

According to an advantageous embodiment, said rod has, at its distal end, a bevel defining a surface inclined with respect to a longitudinal plane, ending at a stub extending perpendicular to the longitudinal axis. Preferably, said applicator comprises a loader able to be mounted on the distal end of an endoscope. According to an advantageous embodiment, said applicator comprises a dorsal part defining a reception surface, the cross section of which corresponds to the cross section defined by the interior edges of the two arms of a staple, the loader further comprising an arch engaged on this dorsal part and guided by two lateral flutes. The staple is in the general form of a horseshoe. The staple has two arms connected by a connecting zone, the distal surface of which has a shape complementary to that of the proximal surface of a stub provided at the distal end of a rod able to move with respect to a sleeve.

The invention also relates to an endoscopic applicator comprising a loader for transversely disposed staples, characterised in that it comprises a movable member having a means for holding a staple to be applied, disposed in a transverse plane, and for ensuring deformation thereof by folding with respect to the symmetry axis of said staple, said control member consisting of a rigid hollow tubular sleeve and a rigid rod sliding longitudinally inside this sleeve, having a guide channel with a complementary cross section. Preferably, the applicator has a dorsal part defining a reception surface, the cross section of which corresponds to the cross section defined by the interior edges of the two arms of a staple, the loader further comprising an arch engaged on this dorsal part and guided by two lateral flutes. The invention also relates to a staple for such a system, characterised in that it has two arms connected by a connecting zone, the distal surface of which has a shape complementary to that of the proximal surface of the stabilisation stub.

BRIEF DESCRIPTION OF THE DRAWINGS

The present invention will be understood better from a reading of the following description, referring to the accompanying drawings, where.

DETAILED DESCRIPTION

Description of the Control Member

Figure 1:
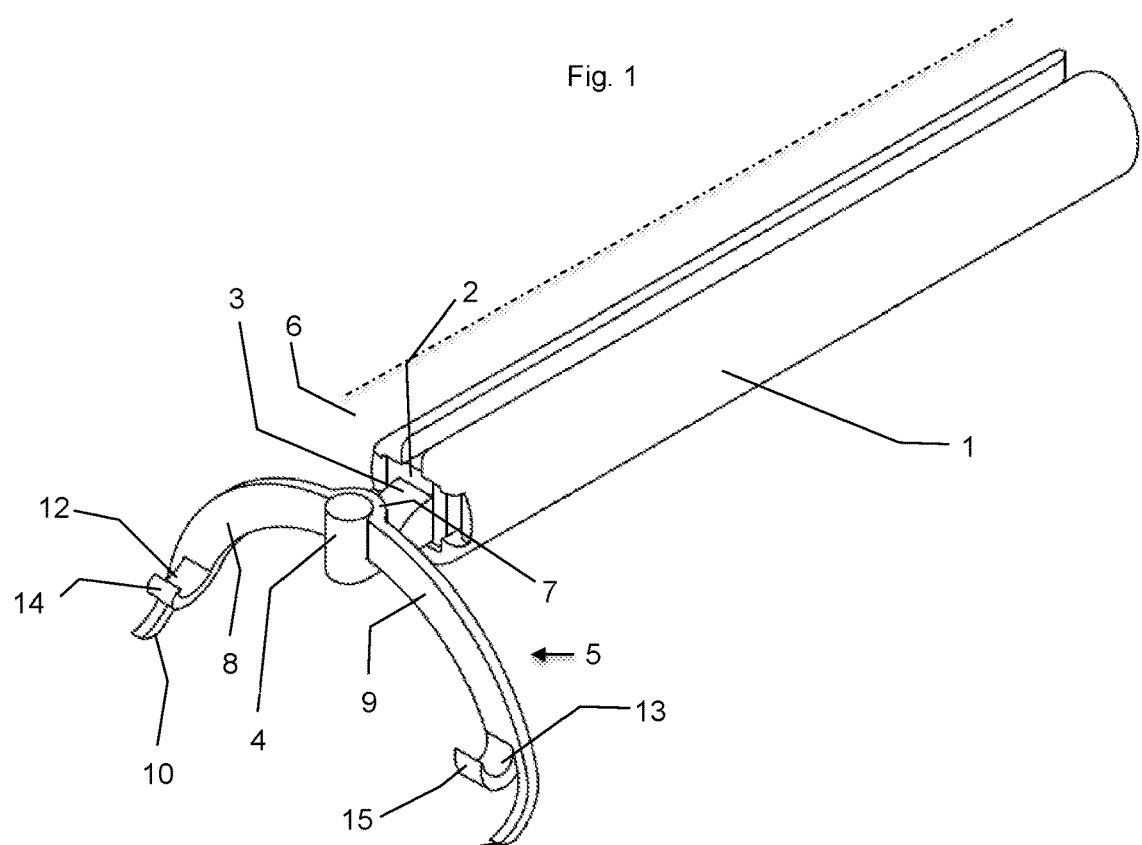
FIG. 1 shows a view of the control member loaded with a staple.

The control member comprises a rigid hollow tubular sleeve (1). A rigid rod (2) with a polygonal cross section slides longitudinally inside this sleeve (1), having a guide channel with a complementary square cross section. This sleeve (1) has at its distal end a bevel (3) defining a surface inclined with respect to a longitudinal plane, ending in a stub (4) extending perpendicularly to the longitudinal axis. The bevel (3) and the stub (4) form a zone receiving a staple (5) having the rough shape of a "horseshoe".

Description of the Staple

The staple has a roughly semi-annular or "horseshoe" shape, in front view and before stapling. In the example described, the staple is formed by a steel cutout but it may also be formed by forming a metal wire or from a biodegradable material. It has two arched arms (8, 9) extending in a transverse plane perpendicular to the longitudinal axis of the sleeve (1), symmetrically with respect to a mid-plane (6) passing through the middle of a connecting portion (7). This mid-plane (6) is defined by an axis parallel to the longitudinal axis of the sleeve (1) and by the axis of the stub (4).

The connecting portion (7) designates simply the part lying between the two arms (8, 9). There is no separation between this zone referred to as the connecting portion (7) and the arms (8, 9) in the example described. However, providing a zone (7) connected by the folding lines to the arms (8, 9) can be envisaged in other embodiments.

This middle portion (7) has a semi-tubular form and is produced by deformation of the material towards the rear with a cylindrical die. The semi-tubular form of the middle portion (7) allows positioning of a guide member provided at the end of an endoscopic instrument, in order to facilitate manipulation of the staple at the time of the placing thereof. Each of the two arms (8, 9) has a pointed end (10, 11) in the form of a hook, extending in front of the transverse plane containing the corresponding arm (8, 9).

The tangent to the pointed end (10, 11) forms, with respect to the normal to the transverse plane, an angle greater than 0° and less than 90°, and preferably between 5° and 50°. This pointed end makes it possible to hook onto the tissues in the vicinity of the area where the staple is placed, and to exert a lateral traction in order to bring them together before stapling. When the angle formed by the tangent is large, dragging of the tissues without perforating them is favoured. If the angle is smaller, penetration of the pointed end in the tissues is favoured.

The two arms (8, 9) also each carry a hook (12, 13) projecting in front of the transverse plane and positioned closer to the pointed end (10, 11) than to the connecting zone (7). The pointed attachment end (10, 11) and the hook (12, 13) can be produced so as to form a split end of the arm (8, 9), one of the tongues of this split end forming the attachment point (10, 11) and the other forming the hook (12, 13). In the example described, the uncoiled length of the attachment point (10, 11) is substantially equal to the uncoiled length of the hook (12, 13). This hook (12, 13) has a gripping surface (14, 15) substantially parallel to the transverse plane. This gripping surface (14, 15) will bear on either side of the tissues at the time of stapling, in order to ensure holding thereof without perforating them.

The functioning of the staple is as follows: the staple is positioned against the two lips to be stapled with an applicator. The staple is in the open position, and the two pointed ends (10, 11) fit flush with the tissues on either side of the separation line of the two lips. These pointed ends (10, 11) slightly penetrate the tissues and hook onto them in order to bring them together when the staple begins to be closed by an instrument making the two arms (8, 9) pivot with respect to the median axis passing through the tubular part of the transverse zone (7). The pointed ends (10, 11) then make a sweeping movement in an arc of a circle, which brings the tissues at the edge of the lips between the two arms, between the two hooks (12, 13). When the two arms are folded against each other, the gripping surfaces (14, 15) hold the edges of the lips in position.

Interaction Between the Sleeve (2) and the Staple (5)

The sleeve (2) has, at its distal front end, two lateral recesses (3, 4), the height of which corresponds to the width of the arms (8, 9) of the staple (5). In addition, the height of the connecting zone (7) is slightly less than the cross section of the channel formed in the tube (1). The stub (4) has a radius of curvature corresponding substantially to the internal radius of curvature of the connecting zone (7).

When the rod (2) is moved longitudinally with respect to the sleeve (1), the staple (5) is applied against the distal front wall of the sleeve (1) and the two arms (8, 9) engage in the lateral recesses (3, 4). By continuing the application of a longitudinal force, these arms (8, 9) are deformed, which causes a closure of the staple. The tips (11, 12) hook on and move the tissues, which come to be positioned between the gripping surfaces (14, 15) of the hooks (11, 12) in order to hold the tissues.

Description of the Staple Loader

Figure 2:
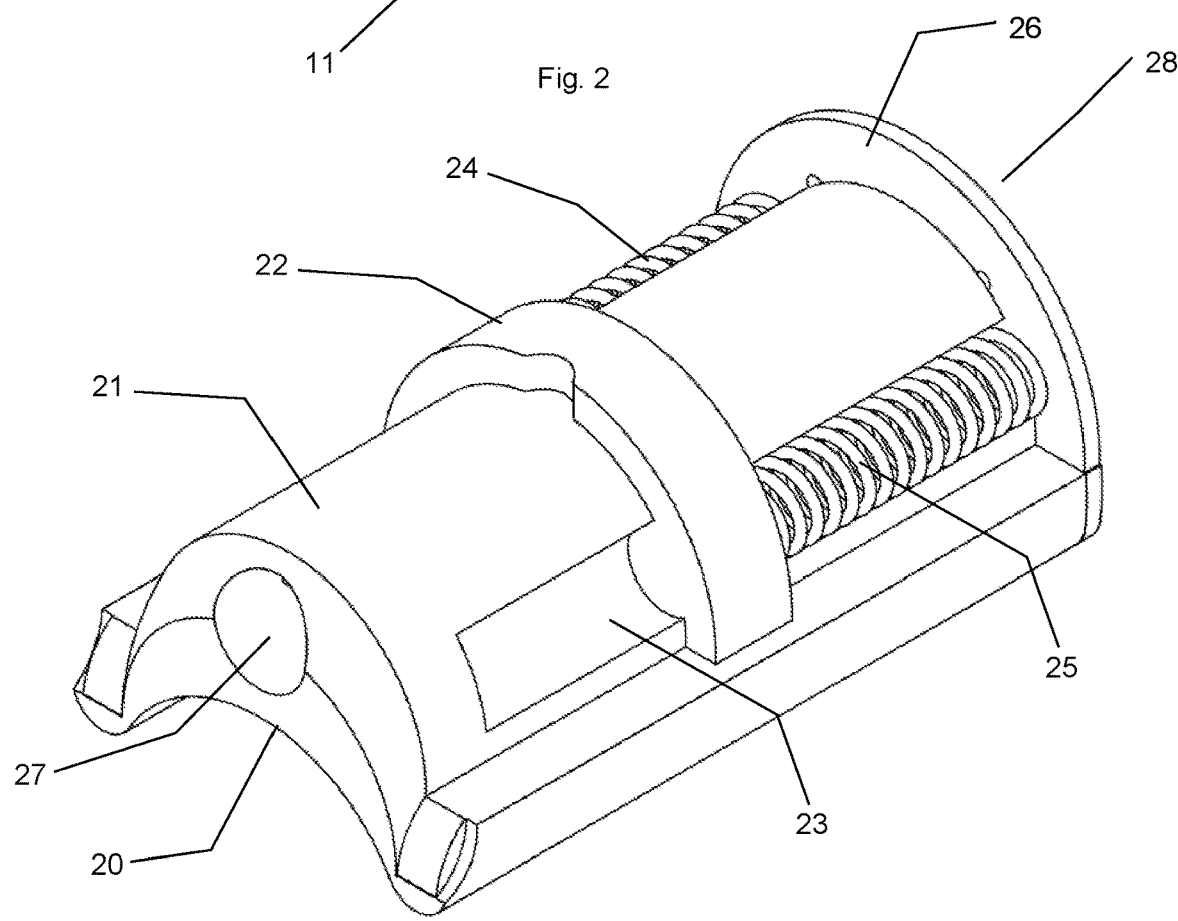
FIG. 2 depicts a view of the staple loader.

FIG. 2 shows an example embodiment of a multistaple loader for an applicator according to the invention. It consists of a housing (20) in the form of a tile, having a ventral surface complementary to the external surface of an endoscope. It can thus be fitted to a standard endoscope, in order to benefit from the lighting and visual examination means, and optionally aspiration means, integrated in such an endoscope.

The dorsal part (21) has a semitubular form, defining an enveloping surface the cross section of which corresponds to the cross section defined by the internal edges of the two arms (8, 9) of a staple (5). The staples can thus be positioned on this dorsal part (21). An arch (22) is engaged on this dorsal part (21) and guided by two lateral flutes (23). This arch (22) is able to move longitudinally, under the action of two springs (24, 25), bearing on a proximal front collar (26).

The loader moreover has a tubular recess (27) extending longitudinally, for introducing the previously described sleeve (1). The staples are all placed transversely and adjacently to form a series of staples (5) parallel to one another. The connecting zone (7) has a protrusion adjacent to that formed by the hooks (13, 14), which makes it possible to maintain parallelism between the consecutive staples.

Functioning of the Applicator

Figure 3:
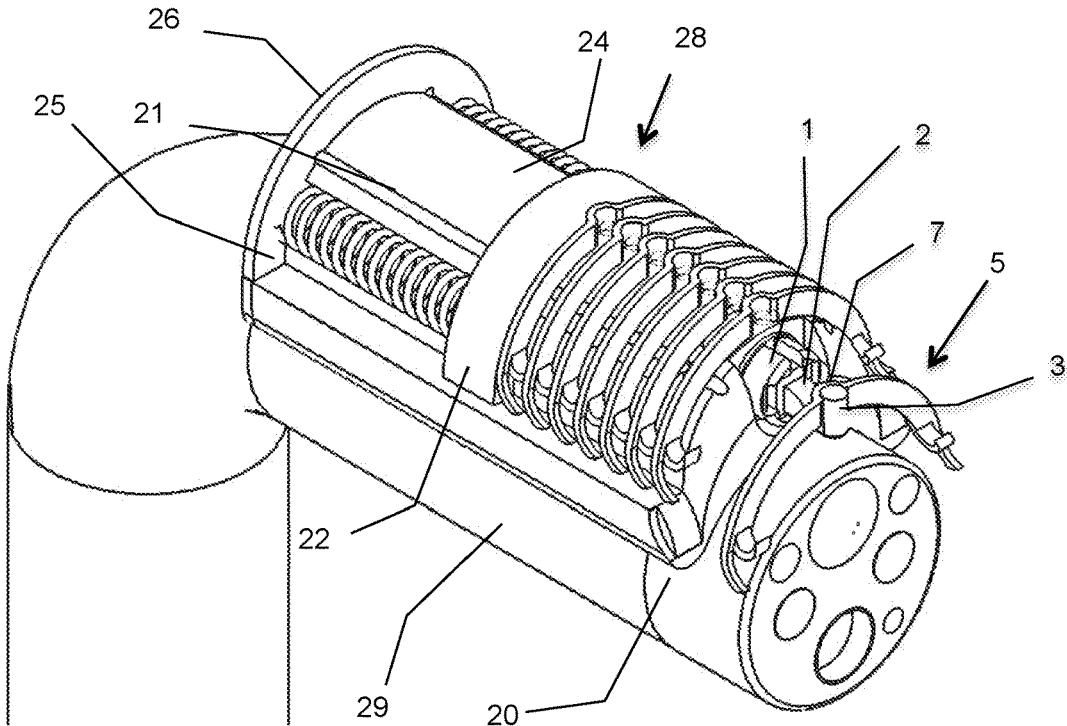
FIGS. 3 to 6 show views of the applicator at various operating steps.

The loader (28) is placed straddling the distal end of the endoscope (29). The rod (2) is pushed slightly out of the sleeve (1). The staple (5) at the distal front end of the series of adjacent staples is pushed by the action of the arch (22) and comes to be housed in the reception zone of the rod (2) as shown in FIG. 3. The other staples are held in place around the dorsal zone (21) of the loader (28) by friction. The connecting zone (7) is placed behind the stub (4), that is to say on the same side as the proximal end (on the operator side), whereas the stub is on the same side as the distal end (on the same side as the tissues to be held).

Figure 4:
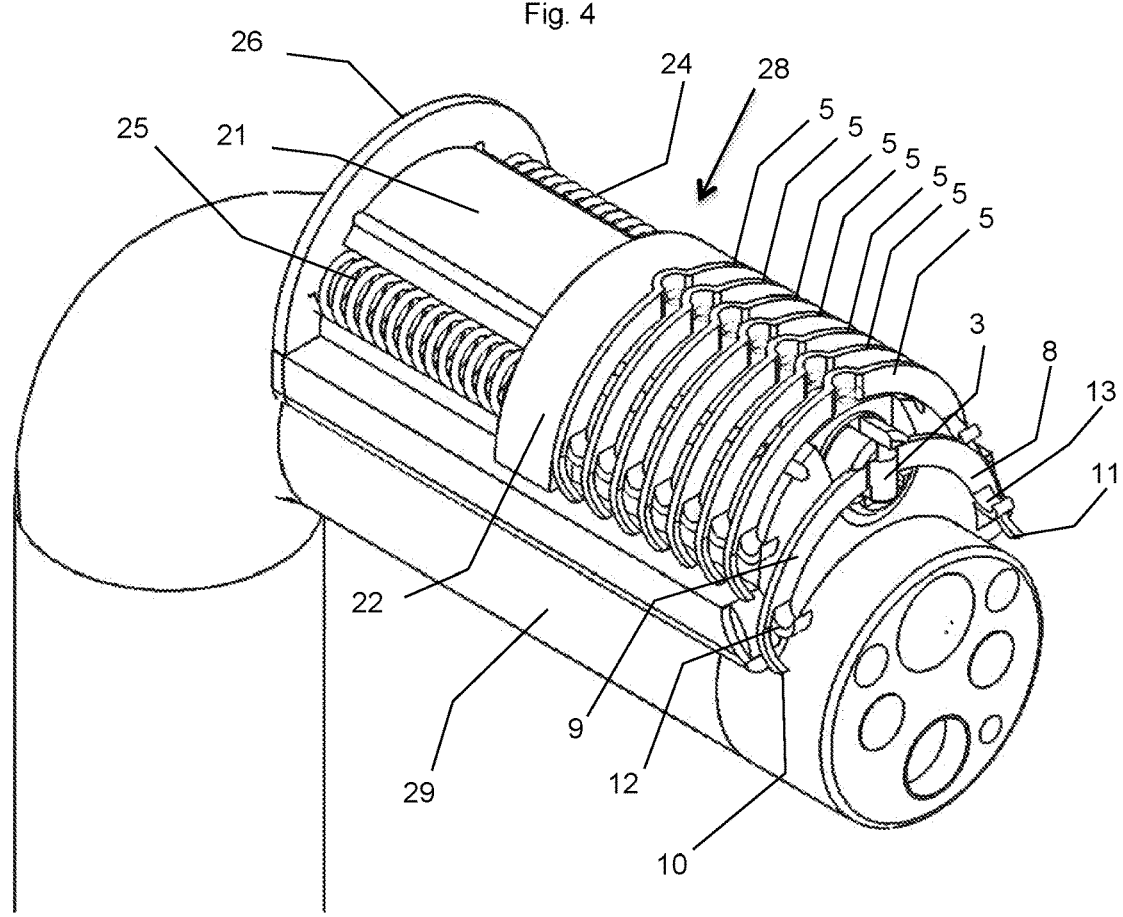
Figure 5:
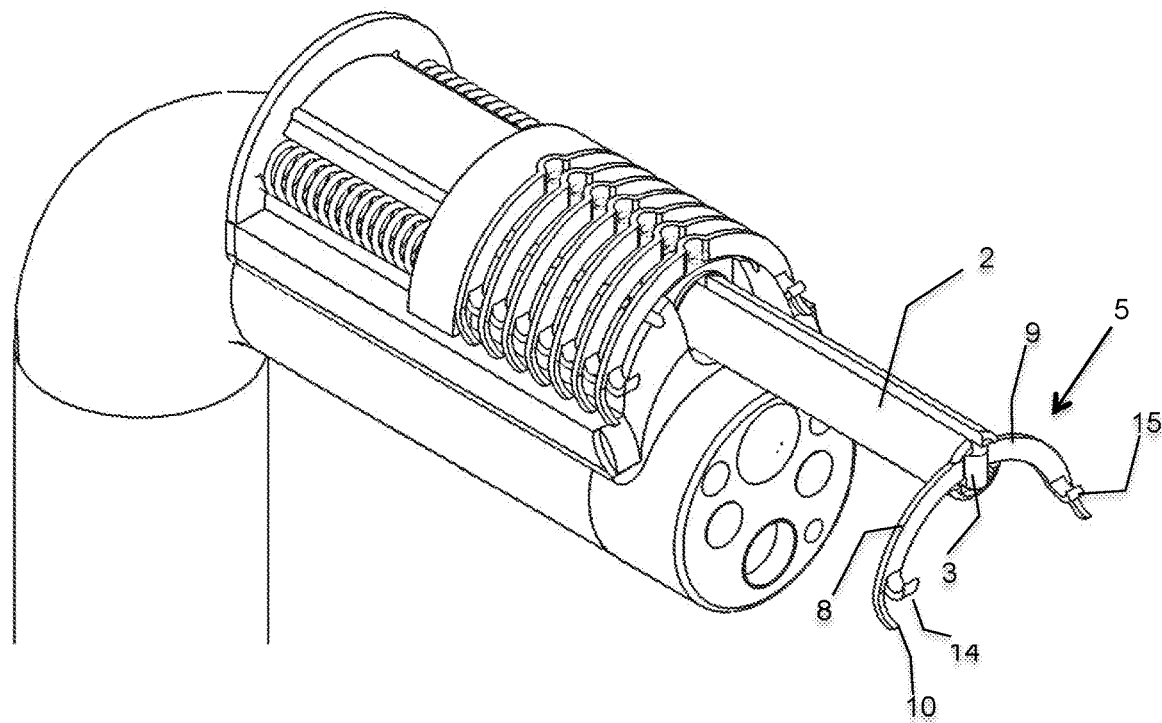
Figure 6:
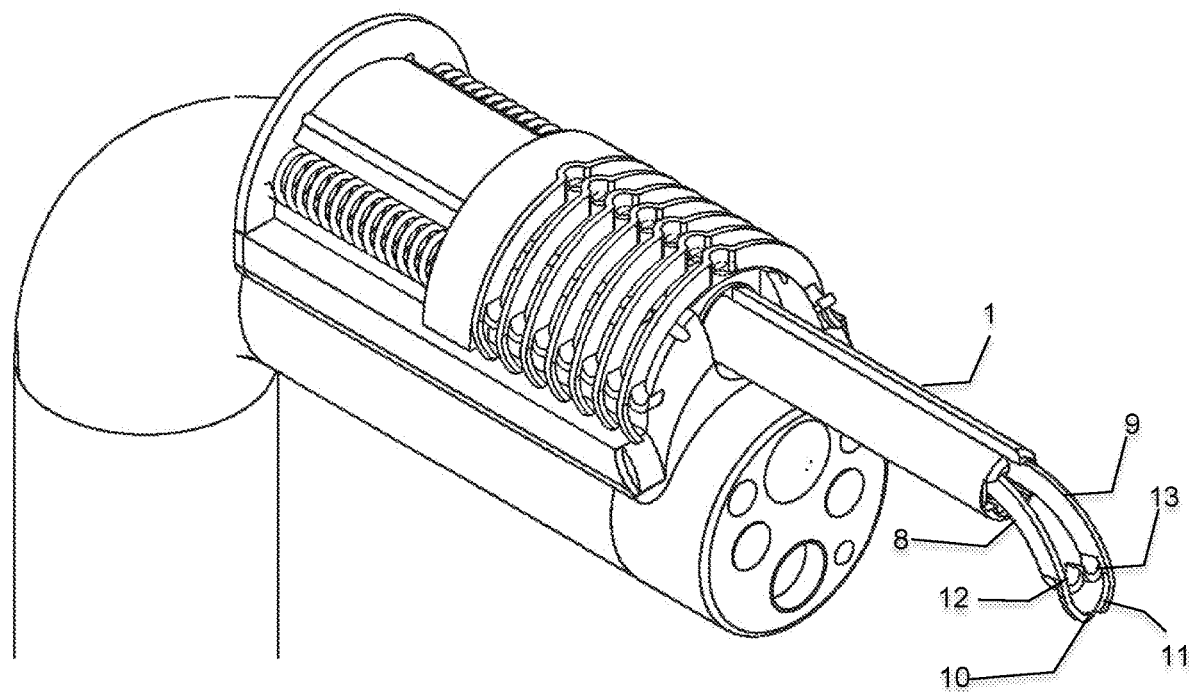

Next the rod (2) is withdrawn inside the sleeve (1) as shown in FIG. 4. The arms (8, 9) then engage in the lateral recesses provided at the front end of the sleeve (1). The staple (5) is then wedged between the stub (4) and the front surface of the sleeve (1), and can be manipulated by the conjoint movement of the sleeve (1) and rod (2). It is thus possible to move the staple by an external action in longitudinal axial movement and in rotation about the longitudinal axis, as shown in FIG. 5. During the longitudinal movement, the points (10, 11) come to fit flush with the tissues, in the field of vision of the endoscope, and hook onto the tissues to be brought together.

By next moving the tube (2) with respect to the sleeve (1), which produces the deformation of the two arms (8, 9), which bend in order to come into a parallel position, to grip the tissues between the hooks (12, 13). While the arms (8, 9) are folded against each other, the pointed ends (10, 11) drag the tissues on a semicircular path, in order to position them between the hooks (12, 13). The user can then lower another staple onto the movable rod by retracting the sleeve and the rod and thus recommence the cycle for placing a new staple. By virtue of the means for longitudinal movement of the staple and the transverse position of the staple (5) once it is loaded onto the holding means, the applicator can advantageously be disposed on an endoscope retracted from the end of the latter so that the device does not enter the field of vision of the endoscope but so that the ends of the arms (8, 9) of the staple (5) enter the field of vision of said endoscope.

The invention claimed is:

1. An endoscopic surgery system comprising a plurality of staples and an endoscopic applicator comprising a loader configured to receive said staples which are transversely disposed relative to said endoscopic applicator, said staples have a central zone and two lateral arms, said endoscopic applicator including a stub holding a staple in a transverse plane relative to said endoscopic applicator, said stub providing deformation to said staple by folding said staple with respect to a symmetry axis of said staple,
    wherein said loader comprises a housing able to be mounted on a distal end of an endoscope,
    wherein said loader comprises a dorsal part defining a reception surface, a cross section of said reception surface corresponds to a cross section defined by internal edges of said two arms of said staple, said loader further comprising an arch engaged to said dorsal part and configured to be guided by two lateral flutes when directing one staple of said staples to be positioned proximate to said stub.

2. An endoscopic applicator comprising a loader configured to receive staples which are transversely disposed relative to said loader, a movable member having a holding stub for holding a staple disposed in a transverse plane with respect to said holding stub in order to provide deformation of said staple by folding said staple with respect to a symmetry axis of said staple, a control member including a rigid hollow tubular sleeve and a rigid rod configured to slide longitudinally inside said sleeve, wherein said sleeve has a guide channel with a cross section corresponding to a cross section of said rigid rod,
    wherein said loader includes a dorsal part defining a reception surface, a cross section of said reception surface corresponds to a cross section defined by internal edges of two arms of said staple, said loader further comprising an arch engaged to said dorsal part and configured to be guided by two lateral flutes when directing said staple to be positioned proximate to said holding stub.

3. An endoscopic surgery system comprising:
    a plurality of staples; and
    an endoscopic applicator including a loader mounted on a distal end of a flexible endoscope, such that said endoscopic applicator does not enter a field of vision of said endoscope, said plurality of staples being placed on said loader,
    wherein said plurality of staples have surfaces complementary to an external surface of said flexible endoscope, and
    wherein said loader includes a housing having an arcuate shape ventral surface complementary to said external surface of said flexible endoscope.

4. The endoscopic surgery system according to claim 3, wherein a bottom of said endoscopic applicator and said staples are curved.

5. The endoscopic surgery system according to claim 4, wherein said staples have forward pointing ends.

6. The endoscopic surgery system according to claim 3, wherein said staples are in a position substantially transverse to a longitudinal axis of said flexible endoscope.

7. The endoscopic surgery system according to claim 6, wherein said staples have forward pointing ends.

8. The endoscopic surgery system according to claim 3, further comprising a sleeve and a rod slidably disposed within a guide channel of said sleeve, said rod having a polygonal cross section that corresponds to a polygonal cross section of said guide channel.

9. An endoscopic surgery system comprising:
    a loader adapted to contain a series of adjacent staples and to be mounted on a distal end of a flexible endoscope; and
    a control member configured to move between a first position in which said control member positions a first staple of said staples proximate to said distal end of said flexible endoscope and a second position in which said control member positions said first staple a distance away from said distal end of said flexible endoscope,
    wherein when said control member is in said second position, said control member is configured to apply said first staple to a tissue by deforming said first staple,
    wherein said staples have an arched surface corresponding to a curved surface of said flexible endoscope,
    wherein said loader includes a dorsal part defining a reception surface, and a cross section of said reception surface corresponds to a cross section defined by internal edges of two arms of said staples, and
    wherein second staples of said staples are held in place around the dorsal part of the loader.

10. The endoscopic surgery system according to claim 9, wherein said control member includes a sleeve and a rod slidably disposed within a guide channel of said sleeve, said rod having a stub that holds said first staple in a transverse plane with respect to said loader when the control member is in said first position and said second position.

11. The endoscopic surgery system according to claim 10, wherein said stub is located externally to the guide channel prior to the control member deforming said first staple and located within said guide channel when said control member deforms said first staple.

* * * * *